United States Patent
Dhingra et al.

Patent Number: 5,891,901
Date of Patent: Apr. 6, 1999

[54] SUBSTITUTED PYRROLES

[75] Inventors: Urvashi Hooda Dhingra, Nutley; Donna Mary Huryn, Allentown; Dennis Dalton Keith, Montclair; Giuseppe Federico Weber, Cedar Grove, all of N.J.

[73] Assignee: Hoffmann-La Roche Inc., Nutley, N.J.

[21] Appl. No.: 899,913

[22] Filed: Jul. 24, 1997

Related U.S. Application Data

[60] Provisional application No. 60/022,050, Jul. 29, 1996, and provisional application No. 60/048,492, Jun. 3, 1997.

[51] Int. Cl.$^6$ .................. A61K 31/40; C07D 209/04
[52] U.S. Cl. .................. 514/414; 514/415; 514/422; 514/427; 548/455; 548/466; 548/469; 548/517; 548/518; 548/530
[58] Field of Search ...................... 514/414, 415, 514/422, 427; 548/455, 466, 469, 517, 518, 530

[56] References Cited

U.S. PATENT DOCUMENTS

| | | | |
|---|---|---|---|
| 5,057,614 | 10/1991 | Davis et al. | 548/466 |
| 5,380,746 | 1/1995 | Barth et al. | 514/414 |

FOREIGN PATENT DOCUMENTS

| | | |
|---|---|---|
| 05039289 | 5/1993 | Japan . |
| WO 93/18765 | 9/1993 | WIPO . |
| WO 93/24491 | 12/1993 | WIPO . |

OTHER PUBLICATIONS

"Inhibitors of Protein Kinase C. 1. 2,3–Bisarylmaleimides," Peter D. Davis et al., *J. Med. Chem.*, 1992, 35, pp. 177–184.
Am. J. Hygiene vol. 27, pp. 493–497, 1938.

*Primary Examiner*—Johann Richter
*Assistant Examiner*—Jane C. Osowecki
*Attorney, Agent, or Firm*—George W. Johnston; Patricia S. Rocha-Tramaloni; Robert A. Silverman

[57] ABSTRACT

Compounds of the formula

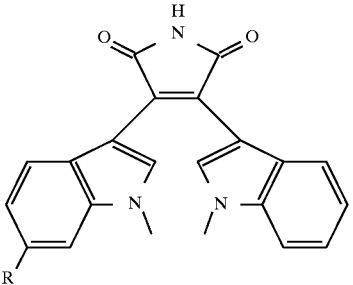

wherein R is alkyl, alkylthio or hydroxy, as well as, pharmaceutically acceptable salts of compounds of formula I are antiproliferative agents useful in the treatment of cancer.

10 Claims, No Drawings

SUBSTITUTED PYRROLES

This application claims the benefit of Provisional Application No. 60/022,080 filed Jul. 29, 1996 and Provisional Application No. 60/048,492 filed Jun. 3, 1997.

BRIEF SUMMARY OF THE INVENTION

The invention relates to substituted pyrroles. More particularly, the invention relates to substituted pyrroles of the formula

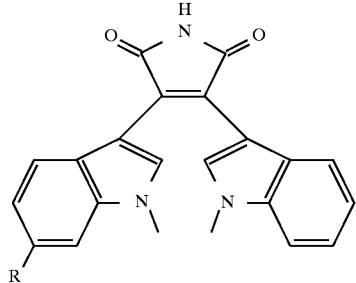

wherein R is alkyl, hydroxy, or alkylthio, as well as pharmaceutically acceptable prodrugs or pharmaceutically acceptable salts of compounds of formula I.

The compounds of formula I and their pharmaceutically acceptable salts are anti-proliferative agents useful in the treatment or control of cancer, particularly in the treatment or control of solid tumors. The compounds of the invention are especially useful in the treatment or control of breast and colon tumors.

DETAILED DESCRIPTION OF THE INVENTION

The invention relates to substituted pyrroles. More particularly, the invention relates to substituted pyrroles of the formula

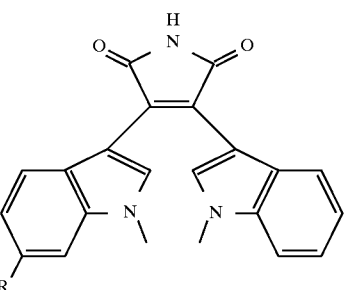

wherein R is alkyl, hydroxy, or alkylthio, as well as pharmaceutically acceptable prodrugs or pharmaceutically acceptable salts of compounds of formula I.

Compounds of formula I are generically disclosed in U.S. Pat. No. 5,057,614.

As used herein, the term "alkyl", alone or in combination means a straight or branched-chain alkyl group containing a maximum of 10, preferably a maximum of 5 carbon atoms, such as, methyl, ethyl, propyl, isopropyl and the like which is unsubstituted or substituted by one or more substituents selected from the group consisting of hydroxy, alkoxy, amino, halogen, cyano, thioalkyl, carboxy, carboxylic acid derivative or alkylsulphinyl. Preferably, alkyl is unsubstituted alkyl, more preferably methyl. The term "hydroxy protecting group" means any conventional hydroxy protecting group such as methylsulfanyl, acetyl, trialkylsilyl, benzyl. Preferably, the hydroxy protecting group is methylsulfanyl.

The term "pharmaceutically acceptable prodrugs" means a compound that may be converted under physiological conditions or by solvolysis to a compound of the formula I or to a pharmaceutically acceptable salt thereof.

In formula I above, R is preferably $CH_3$, OH or $SCH_3$.

The compounds of formula I, as well as, pharmaceutically acceptable salts of compounds of formula I are prepared by the following Schemes 1 and 2.

SCHEME 1

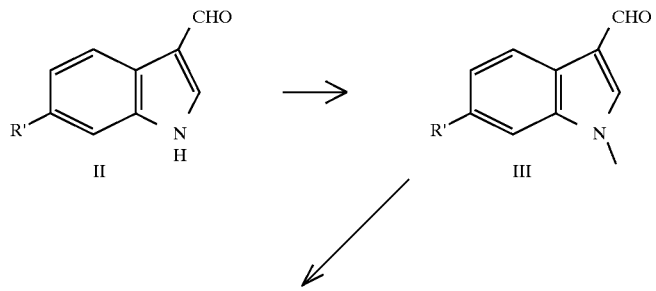

-continued
SCHEME 1

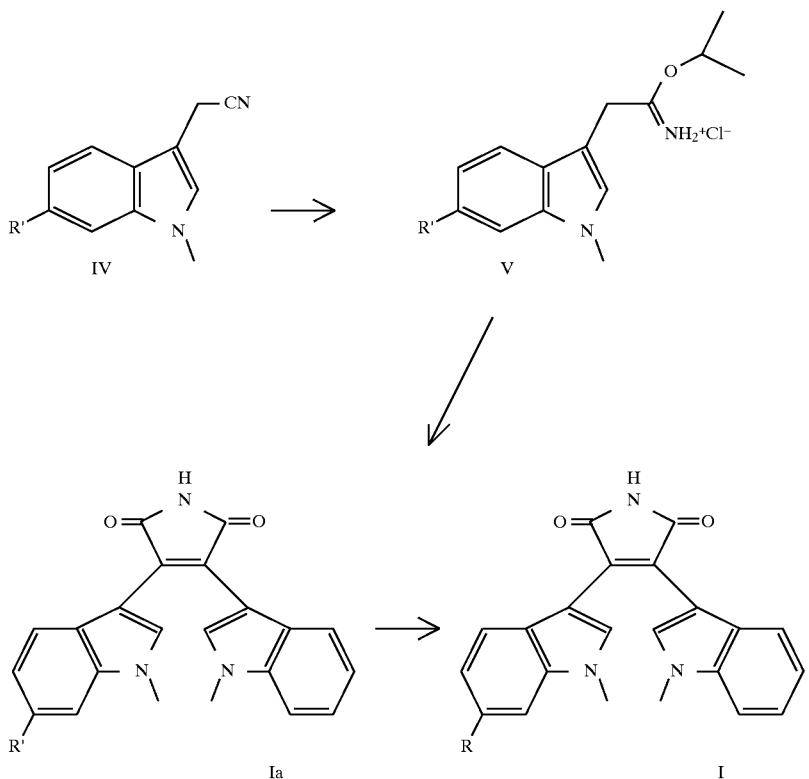

wherein R is as described above and R' is alkyl, alkylthio or OX wherein X is a hydroxy protecting group.

As set forth in Scheme 1, the compound of formula II, a known compound or compound prepared by known methods is reacted to form a corresponding compound of formula III with a base such as sodium hydride (NaH) and alkylating agent such as methyl iodide (CH₃I) in a solvent such as N,N-dimethylformamide (DMF) or tetrahydrofuran (THF) at a temperature of from 0° to 25° C.

A compound of formula III is reacted with a mixture of toluene-4-sulfonylmethyl isocyanide (TosMIC) and potassium tert-butoxide in a solvent such as ethylene glycol-dimethyl-ether(DME) at a temperature between −30° C. and −60° C., then treated with methanol at a temperature of 65° C. to form a corresponding compound of formula IV.

A compound of formula IV is reacted with HCl gas in isopropanol at a temperature of 0° C. to form a corresponding compound of formula V.

A compound of formula V is reacted with (1-methyl-1H-indol-3-yl)-oxo-acetylchloride and triethylamine (Et₃N) in a solvent such as methylene chloride at a temperature of between 0° and 25° C. The resultant product is then treated with para-toluenesulphonic acid (pTsOH) in a solvent such as toluene at a temperature of 25° C. to form a corresponding compound of formula Ia.

The compound of formula Ia wherein R' is OX is converted to a compound of formula I wherein R is hydroxy by removal of the hydroxy protecting group by conventional means, such as treatment with a base such as sodium hydroxide in an aqueous/alcohol solution.

Alternatively, a compound of formula I is prepared as set forth in Scheme 2.

SCHEME 2

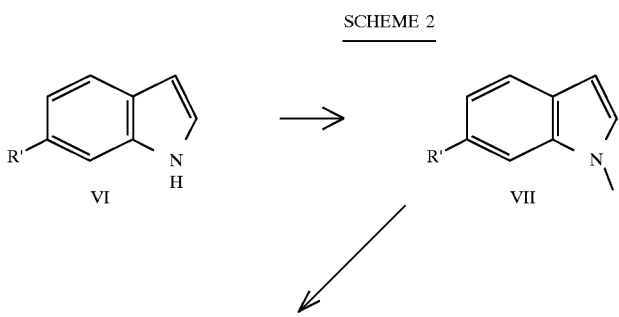

-continued
SCHEME 2

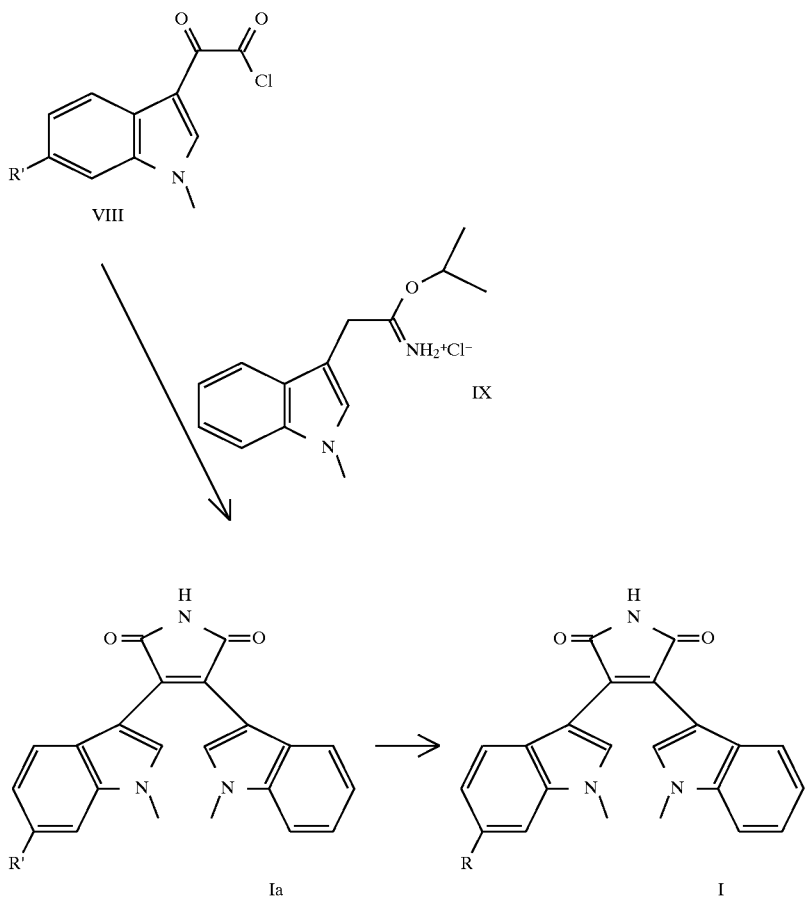

wherein R and $R^1$ are as described above.

As set forth in Scheme 2, a compound of formula VI, a known compound or compound prepared by known methods, is reacted to form a corresponding compound of formula VII with NaH and $CH_3I$ in a solvent such as DMF or THF.

A compound of formula VII is reacted with oxalyl chloride in a solvent such as diethyl ether ($Et_2O$) or dichloromethane ($CH_2Cl_2$) to form the corresponding compound of formula VIII.

A compound of formula VIII is reacted with a compound of formula IX, a known compound or compound prepared by known methods, and pTsOH in $CH_2Cl_2$ at 0°–25° C. followed by reaction with $Et_3N$ in a solvent such as toluene at about 25° C. to form a corresponding compound of formula Ia. The compound of formula Ia wherein R' is OX is converted to the compound of formula I wherein R is hydroxy by removal of the hydroxy protecting group by conventional methods, such as, treatment with NaOH in aqueous/alcohol solvent mixtures.

The compounds of formula I and their pharmaceutically acceptable salts inhibit cellular processes, for example, cell proliferation and are thus useful in the treatment or control of cancer, inflammatory diseases, immunological and bronchopulmonary and cardiovascular disorders and in conjunction with organ transplants.

The antiproliferative activity of the compounds of the invention is demonstrated below. These effects indicate that the compounds are useful in treating cancer.

The epithelial breast carcinoma cell line, MDA-MB435 and the colon carcinoma cell line, SW480, were purchased from ATCC (American Type Culture Collection) and were grown in culture in medium as recommended by ATCC. For analysis of the effect of various compounds on growth of these cells, the cells were plated at a concentration of 1500 cells/well in a 96 well tissue culture plate ("test plate"). The day after the cells were plated, the compounds to be analyzed were dissolved in 100% DMSO (dimethyl sulfoxide) to yield a 10 mM stock solution. Each compound was diluted in $H_2O$ to 1 mM and was added to triplicate wells in the first row of a 96 well master plate which contains medium to yield a final concentration of 40 $\mu M$. The compounds were then serially diluted in medium in the "master plate". The diluted compound(s) were then transferred to test plates containing cells. A row of vehicle "control cells" received DMSO. The final concentration of DMSO in each well was 0.1%. At day 5 post-drug addition, the plate containing MDA-MB435 cells were analyzed as follows. Plates containing SW480 cells were analyzed at day 7 post-drug addition as follows.

MTT ([3-(4,5-dimethylthiazole-2-yl)-2,5-diphenyl-2H-tetrazolium bromide]; thiazolyl blue) was added to each well to yield a final concentration of 1 mg/ml. The plate was then incubated at 37° C. for 2½–3 hours. The MTT containing medium was then removed and 50 $\mu l$ of 100% ethanol was added to each well to dissolve the formazan. The absorbences were then read using an automated plate reader (Bio-tek microplate reader). $IC_{50}$'s were calculated using the Reed and Munsch equation, see, Am. J. Hygiene Vol. 27 pgs. 493–497, 1938.

The results are set forth in Table I below.

TABLE I

Antiproliferative Activity

| Compound | Cell Line | |
|---|---|---|
| | MDAMB435 $IC_{50}$ ($\mu M$) | SW480 $IC_{50}$ ($\mu M$) |
| Compound A | 0.033* | 0.029* |
| Compound B | 0.045* | 0.07* |
| Compound C | 0.03 | 0.07* |
| Compound D | 0.08* | — |
| Compound E | 0.2 | — |

* An average of two separate experiments

Compound A is 3-(1,6-dimethyl-1H-indol-3-yl)-4-(1-methyl-1H-indol-3yl)-pyrrole-2,5-dione.

Compound B is 3-(6-methylsulfanyl-1-methyl-1H-indol-3-yl)-4-(1-methyl-1H-indol-3-yl)-pyrrole-2,5-dione.

Compound C is 3-(6-hydroxy-1-methyl-1H-indol-3-yl)-4-(1-methyl-1H-indol-3-yl)-pyrrole-2,5-dione.

Compound D is 3-(6-ethyl-1-methyl-1H-indol-3-yl)-4-(1-methyl-1H-indol-3-yl)-pyrrole-2,5-dione.

Compound E is {1-methyl-3-[4-(1-methyl-1H-indol-3-yl)-2,5-dioxo-2,5-dihydro-1H-pyrrol-3-yl]-1H-indol-6-yl}-acetonitrile.

The pyrroles of formula I and their aforementioned salts can be used as medicaments, for example, in the form of pharmaceutical preparations, which can be administered orally, for example, in the form of tablets, coated tablets, dragees, hard or soft gelatin capsules, solutions, emulsions or suspensions. They can also be administered rectally, for example, in the form of suppositories or parenterally, for example, in the form of injection solutions.

For the manufacture of pharmaceutical preparations these compounds can be formulated with therapeutically inert, inorganic or organic carriers. Lactose, maize starch or derivatives thereof, talc, steric acid or its salts can be used as such carriers for tablets, coated tablets, dragees and hard gelatin capsules. Suitable carriers for soft gelatin capsules are vegetable oils, waxes, fats, semi-solid or liquid polyols. Depending on the nature of the active substance no carriers are, however, generally required in the case of soft gelatin capsules. Suitable carriers for the manufacture of solutions and syrups are, water, polyols, saccharose, invert sugar and glucose. Suitable carriers for injection are water, alcohols, polyols, glycerine, vegetable oils, phospholipids and surfactants, suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain still other therapeutically valuable substances.

As mentioned above, the pyrroles of formula I and their aforementioned salts can be used in the treatment or control of oncological, inflammatory, immunological, bronchopulmonary and cardiovascular disorders. The dosage can vary within wide limits and will, of course, be adjusted to the individual requirements in each particular case. In general, in the case of oral or parenteral administration to adult humans, a daily dosage of about 5 mg to 5000 mg should be appropriate, although the upper limit may be exceeded when indicated. The daily dosage can be administered as a single dose or in divided doses, or for parenteral administration, it may be given as continuous infusion.

The following Examples illustrate the present invention.

EXAMPLE 1

3-(1,6-dimethyl-1H-indol-3-yl)-4-(1-methyl-1H-indol-3yl)-pyrrole-2,5-dione

A solution of the known 6-methyl-1H-indole-3-carboxaldehyde (5 g, 31 mm) in DMF (100 mL) was cooled to 0° C. and treated with NaH (38 mm), and stirred at 0° C. for 3 hours. After treatment with $CH_3I$ (2.35 mL, 38 mm), the mixture was allowed to warm to room temperature overnight. The mixture was poured into $H_2O$(500 mL) and extracted with ethylacetate (EtOAc) (200 mL×3). The combined organic layers were dried over $MgSO_4$, filtered and evaporated. Purification by flash column chromatography afforded 1,6-dimethyl-1H-indole-3-carboxaldehyde (5.2 g, 97%).

A suspension of potassium tert-butoxide (KOtBu) (2.21 g, 19.7 mm) in DME (30 mL) was cooled to −30° C., and treated with a solution of TosMIC (1.97 g 10.1 mm). After addition was complete, the mixture was further cooled to −60° C., treated with 1,6-dimethyl-1H-indole-3-carboxaldehyde (5.8 mm) in DME(20 mL), and stirred at that temperature for 1.5 hours. Addition of methanol (15 mL) to the cooled solution, was followed by heating to reflux temperature for 15 minutes, and evaporation of the solvent. The residue was treated with $H_2O$ (20 mL) containing acetic acid (HOAc) (0.75 mL), then extracted with $CH_2Cl_2$ (50 mL×3). The combined organic fractions were extracted with saturated $NaHCO_3$ solution, dried over $MgSO_4$, filtered and evaporated. Purification by flash column chromatography afforded (1,6-dimethyl-1H-indol-3-yl)-acetonitrile (0.86 g, 81%).

HCl (gas) was bubbled into a suspension of (1,6-dimethyl-1H-indol-3-yl)-acetonitrile (0.86 g 4.7 mm) in isopropanol (iPrOH) (20 mL), which had been chilled to 0° C., for 3 hours. After evaporation of the solvent, the residue was evaporated from diethylether ($Et_2O$) (50 mL×2), and further dried under high vacuum to yield 2-(1,6-dimethyl-1H-indol-3-yl)-acetimidic acid isopropyl ester hydrochloride.

To a suspension of the known (1-methyl-1H-indol-3-yl)-oxo-acetyl chloride (183 mg, 0.83 mm) and 2-(1,6-dimethyl-1H-indol-3-yl)-acetimidic acid isopropyl ester hydrochloride (233 mg, 0.83 mm) in $CH_2Cl_2$ (6 mL) which had been cooled to 0° C., was added $Et_3N$ (0.46 mL, 3.3 mm). The reaction was allowed to warm to room temperature overnight, then diluted with $CH_2Cl_2$(20 mL), and extracted with $H_2O$(15 mL) and 0.5N HCl(15 mL). The organic fraction was dried over $MgSO_4$, filtered and evaporated, and the residue combined with toluene (3 mL). After cooling to 0° C., para-toluene sulfonic acid (pTsOH) (174 mg, 0.91 mm) was added, and the mixture was stirred at room temperature for 3 hours. The red solids which precipitated were collected and partitioned between $CH_2Cl_2$(50 mL) and $H_2O$(25 mL). The organic fraction was washed with saturated $NaHCO_3$(25 mL) solution, then dried over $MgSO_4$, filtered and evaporated. The residue was washed with cold $CH_2Cl_2$ to yield 3-(1,6-dimethyl-1H-indol-3-yl)-4-(1-methyl-1H-indol-3yl)-pyrrole-2,5-dione; mp=264°–266° C.

EXAMPLE 2

3-(6-methylsulfanyl-1-methyl-1H-indol-3-yl)-4-(1-methyl-1H-indol-3-yl)-pyrrole-2,5-dione a) A solution of 6-methylsulfanyl-1H-indole (6.8 g, 42 mmol) in DMF (50 mL) was added to a slurry of NaH (55 mmol) in DMF(10 mL) at 0° C. over a period of 10 minutes. After stirring for 1 hour at 0° C., CH₃I (4.0 ml,64 mmol) was added and the mixture stirred for 30 minutes at 0° C., then at room temperature for 1 hour, then poured into ice/H₂O and extracted with EtOAc. The organic phase was washed with saturated NaCl solution, dried over MgSO₄, filtered and evaporated to give 6.7 g (91.0%) of 1-methyl-6-methylsulfanyl-1H-indole as a yellow oil after flash column chromatography.

b) To a solution of 1-methyl-6-methylsulfanyl-1H-indole (658 mg, 3.71 mmol) in Et₂O(7 ml) at 0° C., was added oxalyl chloride (0.55 ml, 6.31 mmol). After stirring for 3 hours, the orange solid was collected, washed with Et₂O, and dried to afford (1-methyl-6-methylsulfanyl-1H-indol-3-yl)-oxo-acetyl chloride (819 mg, 66%).

c) To a solution of (1-methyl-6-methylsulfanyl-1H-indol-3-yl)-oxo-acetyl chloride (816 mg, 3.05 mmol) and 2-(1-methyl-1H-indol-3yl)-acetimidic acid isopropyl ester hydrochloride (815 mg, 3.06 mmol) in CH₂Cl₂ (40 mL) at 0° C., was added Et₃N (1.75 ml, 12.56 mmol). After stirring at the same temperature for 30 minutes, the reaction mixture was stirred at room temperature for 3.5 hours, and diluted with CH₂Cl₂. The organic phase was washed with H₂O, 0.5N HCl solution, saturated NaCl solution, then dried over MgSO₄, filtered and evaporated to provide an orange foam. This material was dissolved in toluene (24 ml), and treated with p-TsOH (613 mg, 3.23 mmol) at 0° C. After stirring for 3 hours at room temperature, the reaction mixture was extracted with CH₂Cl₂. The organic phase was washed with a saturated NaHCO₃ solution, saturated NaCl solution, then dried over MgSO₄, filtered and evaporated. Purification via flash column chromatography afforded, 3-(6-methylsulfanyl-1-methyl-1H-indol-3-yl)-4-(1-methyl-1H-indol-3-yl)-pyrrole-2,5-dione (435.8 mg, 35.5%); mp 246°–251° C.

6-methylsulfanyl-1H-indole was prepared as follows:

To a solution of sodium methoxide prepared from Na metal (8.65 g, 0.38 m) in methanol(200 mL) at 0°–5° C., was added a solution of 4-(methylthio)benzaldehyde (12.6 ml, 94.7 mmol) and methyl azidoacetate (44 g, 0.382 mol) in methanol (30 mL). After stirring at the same temperature for 3 hours, the suspension was diluted with H₂O (300 mL). The solids were filtered, washed with water and dried under vacuum to provide 19.4 g (82.0%) of methyl-2-azido-3-(4-methylthiophenyl)propenoate as a yellow solid.

A solution of methyl-2-azido-3-(4-methylthiophenyl)-propenoate (20.6 g, 83 mmol) in xylene (200 ml) was added dropwise to boiling xylene (250 ml) over a period of 2 hours. The reaction mixture was allowed to heat at reflux temperature for an additional 2 hours, then cooled slowly and placed in a freezer overnight. The solids were filtered, washed with a small amount of CH₂Cl₂/hexane (1:3) and dried to give 11.2 g (61.0%) of methyl-6-methylsulfanyl-1H-indole-2-carboxylate.

A mixture of methyl-6-methylsulfanyl-1H-indole-2-carboxylate (11.2 g, 51 mmol) and 2N NaOH (125 ml) was heated to reflux temperature for 30 minutes. The clear solution was cooled, and extracted with EtOAc. The aqueous fraction was acidified with concentrated HCl to pH=1, and the precipitate which formed, was filtered and dried to give 6-Methylsulfanyl-1H-indole-2-carboxylic acid (9.6 g, 91.0%).

A mixture of 6-methylsulfanyl-1H-indole-2-carboxylic acid (9.6 g, 46 mmol), Cu powder (2.1 g, 33 mmol) and quinoline (100 ml) was heated at 215° C. for 3 hours. The mixture was cooled to room temperature, filtered through celite, and the filtrate diluted with H₂O (500 mL). The cooled mixture was acidified with concentrated HCl (pH=1), and extracted with EtOAc. The organic fraction was washed with saturated NaCl solution, dried over MgSO₄, filtered and evaporated to give of 6-Methylsulfanyl-1H-indole (6.8 g, 90%) after purification by flash column chromatography.

EXAMPLE 3

3-(6-hydroxy-1-methyl-1H-indol-3-yl)-4-(1-methyl-1H-indol-3-yl)-pyrrole-2,5-dione Benzenesulfonic acid 1-methyl-1H-indol-6-yl ester was prepared from the known benzenesulfonic acid 1-H-indol-6-yl ester according to the procedure described above for the preparation of 1-methyl-6-methylsulfanyl-1H-indole from 6-methylsulfanyl-1H-indole.

Benzenesulfonic acid-3-chlorocarbonecarbonyl-1-methyl-1H-indol-6-yl ester was prepared from benzenesulfonic acid 1-methyl-1H-indol-6-yl ester according to the procedure described above for the preparation of (1-methyl-6-methylsulfanyl-1H-indol-3-yl)-oxo-acetyl chloride.

Benzenesulfonic acid 1-methyl-3-[4-(1-methyl-1H-indol-3-yl)-2,5-dioxo-2,5-dihydro-1H-pyrrol-3-yl]-1H-indol-6-yl ester was prepared from Benzenesulfonic acid-3-chlorocarbonecarbonyl-1-methyl-1H-indol-6-yl ester and 2-(1-methyl-1H-indole-3yl)-acetimidic acid isopropyl ester hydrochloride according to the procedure described above for the preparation of 3-(6-methyl-sulfanyl- 1-methyl-1H-indol-3-yl)-4-(1-methyl-1H-indol-3-yl)-pyrrole-2,5-dione.

3-(6-hydroxy-1-methyl-1H-indol-3-yl)-4-(1-methyl-1H-indol-3-yl)-pyrrole-2,5-dione was prepared by treating Benzenesulfonic acid 1-methyl-3-[4-(1-methyl-1H-indol-3-yl)-2,5-dioxo-2,5-dihydro-1H-pyrrol-3-yl]-1H-indol-6-yl ester (141 mg 0.28 mm) with 4N NaOH (0.5 mL, 2 mmol) and CH₃OH (4 mL) and heating to reflux temperature for 6 hours. After cooling to room temperature, the reaction mixture was diluted with H₂O, acidified with 2N HCl, and extracted with EtOAc. The organic phase was washed with saturated NaCl solution, dried over MgSO₄, filtered and evaporated to afford, after purification by flash column chromatography 3-(6-hydroxy-1-methyl-1H-indol-3-yl)-4-(1-methyl-1H-indol-3-yl)-pyrrole-2,5-dione (15 mg); mp=279°–282° C.

EXAMPLE 4

{1-Methyl-3-[4-(1-methyl-1H-indol-3-yl)-2,5-dioxo-2,5-dihydro-1H-pyrrol-3-yl]-1H-indol-6-yl}-acetonitrile a) A solution of 3.7 g (23.8 mmole) of 1-methyl-6-cyanoindole, a known compound, in 110 mL of methylene chloride was treated at room temperature with 22.6 mL of a solution of 3M diisobutylaluminum hydride (DIBAL) in hexane. The mixture was stirred at 25° C. for 3 h, added to a mixture of 120 mL of 2N hydrochloric acid and 120 mL of methylene chloride and let stirr for 17 h. at room temperature. The organic layer was separated, washed with water, dried over magnesium sulfate, and chromatographed on a silica gel column giving 2.26 g (60%) of 1-methyl-1H-indole-6-carboxaldehyde as a white solid.

b) A solution of 0.900 g (5.65 mmole) of 1-methyl-1H-indole-6-carboxaldehyde was added to a solution of 2.0 g (10.5 mmole) of toluene-4-sulfonylmethyl isocyanide and 20 mL of 1M potassium t-butoxide solution in 15 mL tetrahydrofuran at −50° C. under stirring. The reaction mixture was stirred at −30° C. for 2 h, treated with 20 mL of methanol and the new mixture stirred for an additional 1 hour at 45°–50° C., poured into ice-water and extracted with ethyl acetate. The organic phase was dried over magnesium sulfate and concentrated to yield (1-methyl-1H-indolyl-6-yl)-acetonitrile.

c) {1-Methyl-3-[4-(1-methyl-1H-indol-3-yl)-2,5-dioxo-2,5-dihydro-1H-pyrrol-3-yl]-1H-indol-6-yl}-acetonitrile; mp=225°–226.5° C. was prepared from (1-methyl-1H-indolyl-6-yl)-acetonitrile. (1-methyl-1H-indolyl-6-yl)-acetonitrile in a manner analogous to Examples 2b and 2c.

EXAMPLE 5

3-(6-Ethyl-1-methyl-1H-indol-3-yl)-4-(1-methyl-1H-indol-3-yl)-pyrrole-2,5-dione a) A mixture of 6.0 g of 6-chloroacetyl-1-pivaloylindole (K. Teranishi, et al., Synthesis 1994, 1018), 5.75 mL of 58% hydriodic acid in 35 mL of acetic acid was stirred at room temperature for 2 days. The reaction mixture was poured in water and the product extracted with ethyl acetate, washed with 5% sodium bicarbonate and water. The organic phase was dried over magnesium sulfate and concentrated to give a dark oil. Purification of this material on a silica gel column gave 3.9 g of 1-(6-acetyl-indol-1-yl)-2,2-dimethylpropan-1-one.

b) 3.9 g of 1-(6-acetyl-indol-1-yl)-2,2-dimethylpropan-1-one dissolved in 13-(6-ethyl-1-methyl-1H-indol-3-yl)-4-(1-methyl-1H-indol-3-yl)-pyrrole-2,5-dione 50 mL of methanol was treated with a solution of sodium methoxide (0.84 g of sodium metal in 20 mL of methanol). The reaction was stirred at room temperature for 1 h, poured into 2N hydrochloric acid/ice and extracted with ethyl acetate. The organic extracts were dried over magnesium sulfate and concentrated to give 1.3 g of 6-acetylindole after chromatographic purification.

c) To a slurry of 0.26 g (6.55 mmole) of NaH (60% oil dispersion) in 10 mL of dried N,N-dimethylformamide, a solution of 6-acetylindole (1.04 g, 6.55 mmole) in 5 mL of dried N,N-dimethylformamide was added at 0°–4° C. After 15 min. stirring at the same temperature, 1.45 g (10.1 mmole) of methyl iodide was added. The new mixture was stirred at the same temperature for 1 hour, poured into ice and water and extracted with ethyl acetate. The organic phase was washed with brine, dried over magnesium sulfate and concentrated to give 1-(1-methyl-1H-indol-6-yl)-ethanone after chromatographic purification on a silica gel column.

d) A mixture of 0.226 g 1-(1-methyl-1H-indol-6-yl)-ethanone, 1.35 mL of 85% hydrazine hydrate, 0.88 g of potassium hydroxide in 15 mL of diethylene glycol was stirred at 62° C. over night. The reaction mixture was cooled, poured into water and extracted with ethyl acetate. The organic phase was washed with water, dried over magnesium sulfate and concentrated to give 0.200 g of 6-ethyl-1-methylindole as a colorless oil after chromatographic purification on a silica gel column.

e) 3-(6-Ethyl-1-methyl-1H-indol-3-yl)-4-(1-methyl-1H-indol-3-yl)-pyrrole-2,5-dione; mp=247°–248° C. was prepared from 6-ethyl-1-methylindole in a manner analogous to Examples 2b and 2c.

EXAMPLE 6

TABLET FORMULATION

| Item | Ingredients | mg/Tablet | | | | | |
|---|---|---|---|---|---|---|---|
| 1 | Compound A* | 5 | 25 | 100 | 250 | 500 | 750 |
| 2 | Anhydrous Lactose | 103 | 83 | 35 | 19 | 38 | 57 |
| 3 | Croscarmellose Sodium | 6 | 6 | 8 | 16 | 32 | 48 |
| 4 | Povidone K30 | 5 | 5 | 6 | 12 | 24 | 36 |
| 5 | Magnesium Stearate | 1 | 1 | 1 | 3 | 6 | 9 |
| | Total Weight | 120 | 120 | 150 | 300 | 600 | 900 |

*Compound A represents a compound of the invention.

Manufacturing Procedure:
1. Mix Items 1, 2 and 3 in a suitable mixer for 15 minutes.
2. Granulate the powder mix from Step 1 with 20% Povidone K30 Solution (Item 4).
3. Dry the granulation from Step 2 at 50° C.
4. Pass the granulation from Step 3 through a suitable milling equipment.
5. Add the Item 5 to the milled granulation Step 4 and mix for 3 minutes.
6. Compress the granulation from Step 5 on a suitable press.

EXAMPLE 7

CAPSULE FORMULATION

| Item | Ingredients | mg/Tablet | | | | |
|---|---|---|---|---|---|---|
| 1 | Compound A | 5 | 25 | 100 | 250 | 500 |
| 2 | Hydrous Lactose | 159 | 123 | 148 | — | — |
| 3 | Corn Starch | 25 | 35 | 40 | 35 | 70 |
| 4 | Talc | 10 | 15 | 10 | 12 | 24 |
| 5 | Magnesium Stearate | 1 | 2 | 2 | 3 | 6 |
| | Total Fill Weight | 200 | 200 | 300 | 300 | 600 |

Manufacturing Procedure:
1. Mix Items 1, 2 and 3 in a suitable mixer for 15 minutes.
2. Add Items 4 & 5 and mix for 3 minutes.
3. Fill into a suitable capsule.

EXAMPLE 8

INJECTION SOLUTION/EMULSION PREPARATION

| Item | Ingredient | mg/mL |
|---|---|---|
| 1 | Compound A | 1 mg |
| 2 | PEG 400 | 10–50 mg |
| 3 | Lecithin | 20–50 mg |
| 4 | Soy Oil | 1–5 mg |
| 5 | Glycerol | 8–12 mg |
| 6 | Water | q.s. 1 mL |

Manufacturing Procedure:
1. Dissolve item 1 in item 2
2. Add items 3, 4 and 5 to item 6 and mix until until dispersed, then homogenize.
3. Add the solution from step 1 to the mixture from step 2 and homogenize until the dispersion is translucent.
4. Sterile filter through a 0.2 um filter and fill into vials.

EXAMPLE 9

| | INJECTION SOLUTION/EMULSION PREPARATION | |
|---|---|---|
| Item | Ingredient | mg/mL |
| 1 | Compound A | 1 mg |
| 2 | Glycofurol | 10–50 mg |
| 3 | Lecithin | 20–50 mg |
| 4 | Soy Oil | 1–5 mg |
| 5 | Glycerol | 8–12 mg |
| 6 | Water | q.s. 1 mL |

Manufacturing Procedure:
1. Dissolve item 1 in item 2
2. Add items 3, 4 and 5 to item 6 and mix until until dispersed, then homogenize.
3. Add the solution from step 1 to the mixture from step 2 and homogenize until the dispersion is translucent.
4. Sterile filter through a 0.2 um filter and fill into vials.

We claim:
1. A compound of the formula

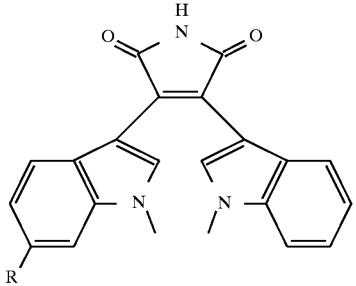

wherein R is alkyl, alkylthio or hydroxy or pharmaceutically acceptable salts of compounds of formula I.

2. A compound of claim 1, wherein R is alkyl.
3. A compound of claim 2, wherein R is unsubstituted alkyl.
4. A compound of claim 3, wherein R is methyl.
5. A compound of claim 1, wherein R is hydroxy.
6. A compound of claim 1, wherein R is alkylthio.
7. A compound of claim 6, wherein R is methylthio.
8. A compound of claim 2, wherein R is alkyl substituted by one or more of hydroxy, alkoxy, amino, halogen, thioalkyl, carboxy, carboxylic acid derivative, cyano or alkylsulphinyl.
9. A compound of claim 8, wherein R is alkyl substituted by cyano.
10. A pharmaceutical composition comprising a compound of formula I.

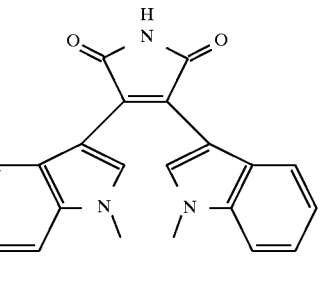

wherein R is alkyl, alkylthio or hydroxy; or pharmaceutically acceptable salts of compounds of formula I and an inert carrier.

* * * * *

UNITED STATES PATENT AND TRADEMARK OFFICE
CERTIFICATE OF CORRECTION

PATENT NO. : 5,891,901
DATED : April 6, 1999
INVENTOR(S) : Dhingra, et al.

It is certified that error appears in the above-identified patent and that said Letters Patent is hereby corrected as shown below:

On the title page item [60], line 1, "Provisional application No. 60/022,050, filed July 29, 1996; and " should read
--- Provisional application No. 60/022,080, filed July 29, 1996; and---.

Signed and Sealed this

Seventeenth Day of August, 1999

Attest:

Q. TODD DICKINSON

*Attesting Officer*     *Acting Commissioner of Patents and Trademarks*